US009661852B1

(12) United States Patent
Bristow

(10) Patent No.: US 9,661,852 B1
(45) Date of Patent: May 30, 2017

(54) SYNERGISTIC HERBICIDAL COMPOSITION AND USE THEREOF

(71) Applicant: ROTAM AGROCHEM INTERNATIONAL COMPANY LIMITED, Chai Wan, Hong Kong (CN)

(72) Inventor: James Timothy Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/958,212

(22) Filed: Dec. 3, 2015

(51) Int. Cl.
*A01N 47/36* (2006.01)
*A01N 41/10* (2006.01)
*A01N 25/12* (2006.01)
*A01N 25/14* (2006.01)

(52) U.S. Cl.
CPC ............. *A01N 47/36* (2013.01); *A01N 41/10* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,481,029 A * | 11/1984 | Levitt | ................. | A01N 47/36 504/212 |
| 5,153,324 A | 10/1992 | Grindstaff | | |
| 5,550,238 A * | 8/1996 | Chiang | ................. | C07D 521/00 544/206 |
| 6,046,134 A * | 4/2000 | De Gennaro | .......... | A01N 41/10 504/133 |
| 6,420,381 B1 * | 7/2002 | Muraoka | ............... | C07D 471/04 514/300 |
| 2010/0152492 A1 | 6/2010 | Binder | | |
| 2015/0031877 A1 * | 1/2015 | Hiratsuka | ............... | A01N 43/84 544/105 |

FOREIGN PATENT DOCUMENTS

| | | | |
|---|---|---|---|
| CN | 101384547 A | | 3/2009 |
| CN | 102265888 | * | 12/2011 |
| CN | 102835412 A | | 12/2012 |
| WO | 9748276 A1 | | 12/1997 |
| WO | WO 2006/021743 | * | 3/2006 |

OTHER PUBLICATIONS

McClurg, R.B., "X-Ray Powder Diffraction (XRPD) to Describe Crystal Forms," Publication of SSCI an Aptuit Company, Jul. 9, 2008, pp. 1-23.*
HCAPLUS abstract 1999:261209 (1999).*
Roberts, R.M. et al. Modern Experimental Organic Chemistry. Holt, Rinehart and Winston, New York, 1979, pp. 49-58.*
HCAPLUS abstract 2011:1593024 (2011).*
Herbicide Handbook, Weed Science Society of America, Seventh Edition—1994, p. 318.
Calculating Synergistic and Antagonistic Responses of Herbicide Combinations; S. R. Colby, Weeds, vol. 15, No. 1 (Jan. 1967), pp. 20-22, Weed Science Society of America and Allen Press.
International Search Report and Written Opinion, mailed Oct. 26, 2016 (PCT/CN2016097658).
International Search Report and Written Opinion, mailed Dec. 12, 2016 (PCT/CN2016098394).
USPTO Office Action, mailed Sep. 20, 2016 (U.S. Appl. No. 14/958,007).
HCAPLUS abstract 2006:1339046 (2006).
Zhao, Bangbin et al., Synthesis of sulfonulurea herbicides using bis(trichloromethyl) carbonate Nongyao, Dec. 31, 2003, No. 7, vol. 42, ISSN:1006-0413, pp. 9-10.
Lu, Yang et al., Synthesis of herbicide thifensulfuron, Xiandai Nongyao, Oct. 31, 2006, No. 5, vol. 5, ISSN: 1671-5284, pp. 22-24.
Zhou, Xinjian et al., The Synthesis Process of Thifensulfuron-methyl, Journal of Nantong Vocational University, Mar. 31, 2014, No. 1, vol. 28, ISSN: 1008-5327, pp. 77-79.

* cited by examiner

*Primary Examiner* — John Pak
(74) *Attorney, Agent, or Firm* — Dickinson Wright PLLC

(57) ABSTRACT

A herbicidal composition is provided, the composition comprising: (A) the crystalline modification I of 2-(4-mesyl-2-nitrobenzoyl)cyclohexane-1,3-dione (mesotrione); and (B) the crystalline modification I of methyl 3-(4-methoxy-6-methyl-1,3,5-triazin-2-ylcarbamoylsulfamoyl)thiophene-2-carboxylate (thifensulfuron-methyl). A method of controlling undesirable plant growth at a locus comprises applying to the locus herbicidally effective amounts of both (A) the crystalline modification I of 2-(4-mesyl-2-nitrobenzoyl)cyclohexane-1,3-dione (mesotrione); and (B) the crystalline modification I of methyl 3-(4-methoxy-6-methyl-1,3,5-triazin-2-ylcarbamoylsulfamoyl)thiophene-2-carboxylate (thifensulfuron-methyl).

32 Claims, 4 Drawing Sheets

SYNERGISTIC HERBICIDAL COMPOSITION AND USE THEREOF

BACKGROUND

1. Field

The present disclosure relates to a synergistic herbicidal composition containing mesotrione and thifensulfuron-methyl, each in particular crystal modifications. The composition finds use in controlling the growth of undesirable plant, particularly in crops, including using the aforementioned composition.

2. Description of Related Art

The protection of crops from undesirable plant, which inhibits crop growth, is a constantly recurring problem in agriculture. To solve this problem, researchers are trying to produce an extensive variety of chemicals and chemical formulations effective in the control of such undesirable growth. Chemical herbicides of many types have been disclosed in the literature and a large number are in commercial use.

Some herbicidal active ingredients have been shown to be more effective when applied in combination rather than applied individually, this effect being referred to as "synergism." According to *Herbicide Handbook* of the Weed Science Society of America, Seventh Edition, 1994, page 318, "synergism" is an interaction of two or more factors such that the effect when combined is greater than the predicted effect based on the response to each factor applied separately.

The compound 2-(4-mesyl-2-nitrobenzoyl)cyclohexane-1,3-dione has the common name "mesotrione". Mesotrione is a substance that can form polymorph crystals. Two different forms, crystalline modifications I and II, of mesotrione are described in WO2006021743, which is incorporated herein by reference for all purposes. Mesotrione is active as a herbicide and is now commercially available in a range of formulations for controlling the growth of undesirable plant. The XRD diffraction data for mesotrione crystal form I from the above publication are given below, although some peak shifting may be possible.

| Peak Position (2-Theta) | Peak Position (d spacing) |
| --- | --- |
| 8.52 | 10.34 |
| 17.08 | 5.18 |
| 17.43 | 5.08 |
| 18.74 | 4.73 |
| 19.04 | 4.66 |
| 19.31 | 4.59 |
| 19.52 | 4.54 |
| 21.15 | 4.20 |
| 25.73 | 3.46 |
| 28.66 | 3.11 |

The compound methyl 3-(4-methoxy-6-methyl-1,3,5-triazin-2-ylcarbamoylsulfamoyl)thiophene-2-carboxylate, having the common name "thifensulfuron-methyl", is a member of the sulfonylurea group of chemicals and used as herbicide. Thifensulfuron-methyl is a selective post-emergence sulfonylurea herbicide for the control of broadleaved weeds in cereals and soybeans. Like other sulfonylureas, the mode of action is via inhibition of the enzyme acetolactate synthase (ALS), and thus prevention of the biosynthesis of the essential amino acids isoleucine and valine.

The commercially available thifensulfuron-methyl, which is usually manufactured by the process described in U.S. Pat. No. 4,481,029, which is incorporated herein by reference, where it is present in an amorphous state.

It has been found that thifensulfuron-methyl in the amorphous state is highly viscous, which is not suitable for being prepared as compositions or formulations having spray equipment cleanout property. Thifensulfuron-methyl residues remain in the spray equipment after spraying. Adequate cleanout prior to reuse of the spray equipment will typically require a rinsing procedure that is not only time-consuming but also results in wastewater disposal problem.

SUMMARY

It has been found that a crystalline form of thifensulfuron-methyl, termed hereinafter "crystalline modification I", has increased solubility, decreased viscosity and improved spray equipment clean-out properties (U.S. Ser. No. 14/958,007, filed on even date herewith, and incorporated herein by reference). The crystalline modification I of thifensulfuron-methyl of the invention exhibits at least 3 of the following reflexes as $2\theta$ values in an X-ray powder diffractogram recorded using Cu—K$\alpha$ radiation at 25° C.:

| | |
| --- | --- |
| $2\theta = 6.62 \pm 0.2$ | (1) |
| $2\theta = 11.11 \pm 0.2$ | (2) |
| $2\theta = 12.84 \pm 0.2$ | (3) |
| $2\theta = 13.30 \pm 0.2$ | (4) |
| $2\theta = 15.48 \pm 0.2$ | (5) |
| $2\theta = 20.04 \pm 0.2$ | (6) |
| $2\theta = 22.34 \pm 0.2$ | (7) |
| $2\theta = 24.62 \pm 0.2$ | (8) |
| $2\theta = 24.92 \pm 0.2$ | (9) |
| $2\theta = 27.83 \pm 0.2$ | (10) |

It has been have surprisingly found that combining the crystalline modification I of mesotrione with the crystalline modification I of thifensulfuron-methyl provides a composition having a synergistic activity, that is, an increased herbicidal activity, compared with the activity expected from the activity of the two components when applied individually.

Accordingly, in a first aspect, the present invention provides a herbicidal composition comprising:

(A) the crystalline modification I of 2-(4-mesyl-2-nitrobenzoyl)cyclohexane-1,3-dione (mesotrione); and (B) the crystalline modification I of methyl 3-(4-methoxy-6-methyl-1,3,5-triazin-2-ylcarbamoylsulfamoyl)thiophene-2-carboxylate (thifensulfuron-methyl).

The composition of an embodiment of the invention is of particular use for controlling the growth of undesirable plant.

In a second aspect, the invention provides a method of controlling the growth of undesirable plant comprising applying to the plant or to the locus thereof a herbicidally effective amount of the herbicidal composition of the first aspect of the present invention.

In a further aspect, the invention provides the use of the herbicidal composition of the first aspect of the invention in control of undesirable plant growth at a locus.

DETAILED DESCRIPTION OF SPECIFIC EMBODIMENTS

Figure 1:
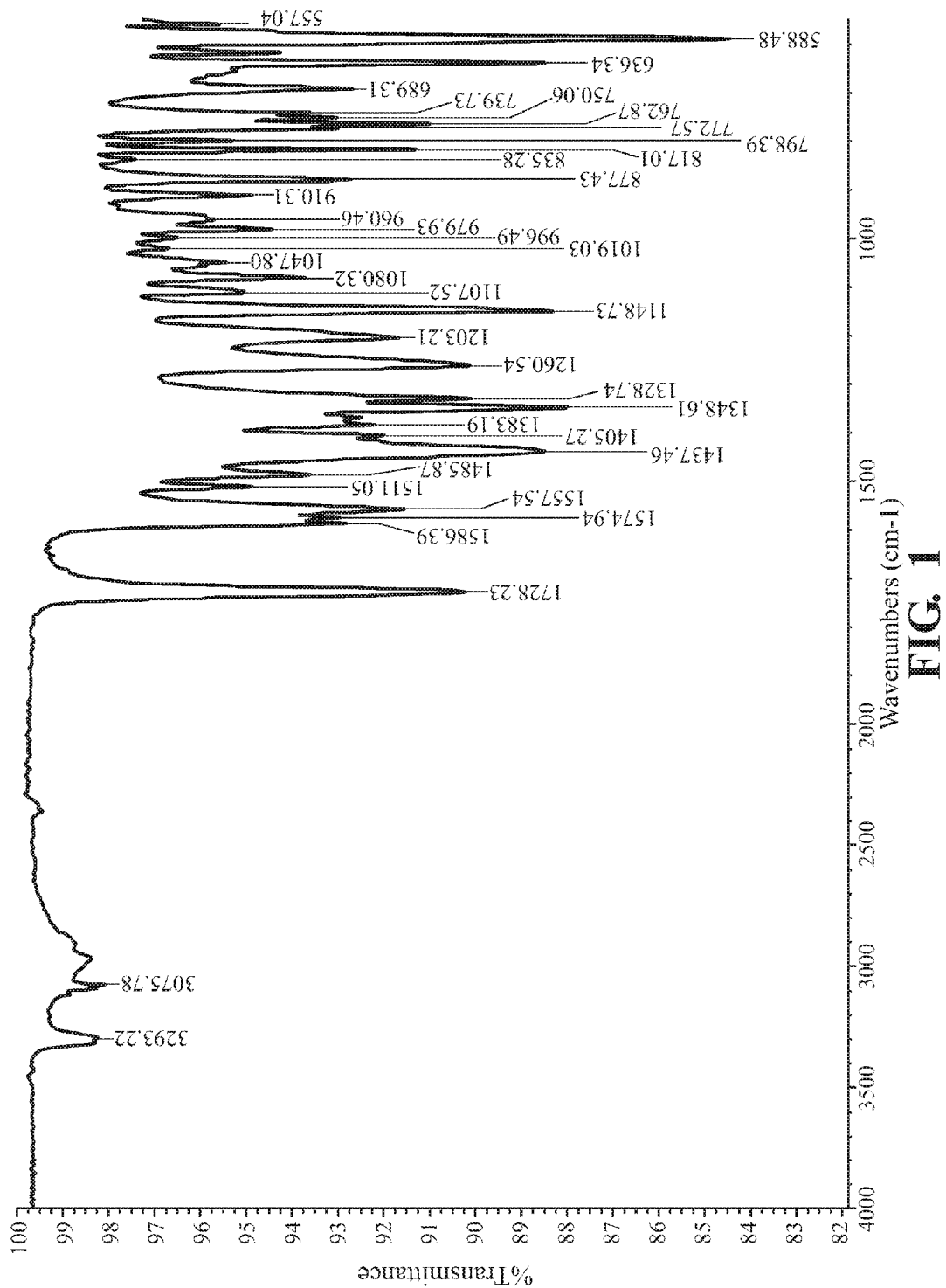
FIG. 1 is an infrared (IR) spectrograph of crystalline modification I of thifensulfuron-methyl, according to an embodiment of the invention.

The references to the crystalline modifications I and II of mesotrione as used herein, refer to the crystalline modification of mesotrione disclosed in WO2006021743, where they are described as Form I and Form II, respectively. The XRD diffraction data for mesotrione crystal form I produced by the process disclosed herein may have a somewhat shifted XRD spectrum, such as:

| Peak Position (2-Theta) | Peak Position (d spacing) |
|---|---|
| 8.44 | 10.47 |
| 17.35 | 5.11 |
| 17.55 | 5.05 |
| 18.67 | 4.75 |
| 18.98 | 4.68 |
| 19.24 | 4.61 |
| 19.45 | 4.56 |
| 21.06 | 4.22 |
| 25.64 | 3.47 |
| 28.55 | 3.13 |

The term "herbicide" as used herein, refers to a compound that controls the growth of plants.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

The term "plants" refers to all physical parts of a plant, including shoots, leaves, needles, stalks, stems, fruit bodies, fruits, seeds, roots, tubers and rhizomes.

The term "locus" refers to the place on which the plants are growing, the place on which the plant propagation materials of the plants are sown or the place on which the plant propagation materials of the plants will be sown.

"At least one" designates a number of the respective compounds or components of 1, 2, 3, 4, 5, 6, 7, 8, 9 or more, preferably 1, 2, or 3.

The synergistic herbicidal composition, the method and use of the present invention are suitable for controlling undesirable plant growth in a range of crops, including: cereals, for example wheat, barley, rye, oats, corn, rice, sorghum, triticale and related crops; fruit, such as pome fruit, stone fruit and soft fruit, such as apples, pears, plums, peaches, pistachio, almonds, cherries, and berries, for example grape, banana, strawberries, bushberry, caneberry, raspberries and blackberries; leguminous plants, for example beans, lentils, peas, and soybeans; oil plants, for example oilseed rape, mustard and sunflowers; cucurbitaceae, for example cantaloupe, marrows, cucumbers, melons, pumpkin, squash and watermelon; fiber plants, for example cotton, flax, hemp, and jute; citrus fruit, such as oranges, lemons, grapefruit and mandarins; and vegetables, for example spinach, lettuce, asparagus, cabbages, carrots, onions, tomatoes, potatoes, paprika, garlic and leeks; coffee; sugarcane; hops; tree nuts; as well as ornamentals, for example flowers, such as roses, shrubs, broad-leaved trees and evergreens, such as conifers. Preferably, the composition described herein is used to treat cereals, sugarcane, leguminous plants, fiber plants and vegetables. More preferably, the composition described herein is used to treat wheat, barley, rye, oats, corn, sorghum, soybean, sugarcane, flax and asparagus.

The control of undesirable plant growth in such crops may be achieved by applying to the locus (A) the crystalline modification I of 2-(4-mesyl-2-nitrobenzoyl)cyclohexane-1, 3-dione (mesotrione), which is identified as Form I in WO 2006/021743 and (B) the crystalline modification I of methyl 3-(4-methoxy-6-methyl-1,3,5-triazin-2-ylcarbamoylsulfamoyl)thiophene-2-carboxylate (thifensulfuron-methyl) in suitable amounts.

The active compounds (A) and (B) may be applied to the locus together or separately. If applied separately, active compounds (A) and (B) may be applied at the same time and/or consecutively. The control may comprise applying to the undesirable plant or the locus thereof a herbicidally effective amount of the herbicidal composition.

It has been surprisingly found that a combination of (A) the crystalline modification I of 2-(4-mesyl-2-nitrobenzoyl) cyclohexane-1,3-dione (mesotrione) and (B) the crystalline modification I of methyl 3-(4-methoxy-6-methyl-1,3,5-triazin-2-ylcarbamoylsulfamoyl)thiophene-2-carboxylate (thifensulfuron-methyl) exhibits a synergistic action in the control of many weeds, particularly, but not limit to, broad-leaved weeds and grasses. For example, weeds treatable according to an embodiment of the invention include:

Indian Mallow (*Abutilon incana*), Velvetleaf (*Abutilon theophrasti*), Hophombeam copperleaf (*Acalypha ostryaefolia*), Virginia Copperleaf (*Acalypha virginica*), Common Yarrow (*Achillea millefolium*), Wild garlic (*Allium ursinum*), Alligatorweed (*Alternantha philoxeroides*), Khakiweed (*Alternanthera pungens*), Pigweed, Tumble (*Amaranthus albus*), Pigweed, Prostrate (*Amaranthus blitoides*), Livid Amaranth (*Amaranthus blitum*), Pigweed, smooth (*Amaranthus hybridus*), Palmer amaranth (*Amaranthus palmeri*), Amaranth, powell (*Amaranthus powellii*), Redroot pigweed (*Amaranthus retroflexus*), Common Waterhemp (*Amaranthus rudis*), Spiny Pigweed (*Amaranthus spinosus*), Amaranth (*Amaranthus* spp), Waterhemp (*Amaranthus tuberculatus*), Huisachedaisy (*Amblyolepis setigera*), Common Ragweed (*Ambrosia artemiisifolia*), Woollyleaf Bursage (*Ambrosia grayi*), Western Ragweed (*Ambrosia psilostachya*), Giant Ragweed (*Ambrosia trifida*), Toothcup (*Ammannia latifolia*), Tarweed fiddleneck (*Amsinckia lycopsoides*), Coast fiddleneck (*Amsinckia menziesii*), Spurred Anoda (*Anoda cristata*), Corn chamomile (*Anthemis arvensis*), stinking mayweed/dogfennel (*Anthemis cotula*), Hemp Dogbane (*Apocynum cannabinum*), Mouse-ear cress (*Arabidopsis thaliana*), Common Burdock (*Arctium minus*), Mexican-Poppy (*Argemone mexicana*), Annual Pricklepoppy (*Argemone polyanthemos*), Silversage (*Artemesia ludoviciana*), Common Milkweed (*Asclepias syriaca*), Antelope Horn (*Asclepias viridis*), Slender Aster (*Aster gracilis*), White Heath Aster (*Aster pilosus*), common orache (*Atriplex patula*), Yellow Rocket (*Barbarea vulgaris*), Kochia(*Bassia scoparia*), Common Beggar-tick (*Bidens alba*), Wild mustard (*Brassica kaber*), black mustard (*Brassica nigra*), Redmaids (*Calandrinia ciliata*), Sprawling Horseweed (*Calyptocarpus vialis*), Smallseed Falseflax (*Camelina microcarpa*), Trumpetcreeper (*Campsis radicans*), Marijuana (*Cannabis*), Hemp (*Cannabis sativa*), Shepherd's purse (*Capsella bursa-pastoris*), Bittercress, smallflowered (*Cardamine parviflora*), Thistle, musk (*Carduus nutans*), Thistle, Distaff (*Carthamus lanatus*), Partridgepea (*Cassia chamaecrista*), SilverLeaf Cassia (*Cassia phyllodinea*), Thistle, Malta Star (*Centaurea melitensis*), Centella (*Centella asiatica*), Mouse-ear chickweed (*Cerastium vulgatum*), Field chickweed (*Cerastium arvense*), Sticky chickweed (*Cerastium glomeratum*), Mouseear Chickweed (*Cerastium vulgatum*), False nightshade (*Chamaesaracha coronopus*), Garden Spurge (*Chamaesyce hirta*), Hyssop spurge (*Chamaesyce hyssopifolia*), fireweed (*Chamerion angustifolium*), Common Lambsquarters (*Chenopodium album*), narrowleaf lambsquarters (*Chenopodium desiccatum*), *Atriplex*(*Chenopodium orach*), Goosefoots (*Chenopodium* spp.), blue/purple mustard (*Chorispora tenella*), Oxeye Daisy (*Chrysanthemum leucanthemum*), Chicory (*Cichorium intybus*), Waterhemlock (*Cicuta maculata*), Thistle, Tall (*Cirsium altissimum*), Canada Thistle (*Cirsium arvense*), Thistle, Texas Purple (*Cirsium texanum*), Bull Thistle (*Cirsium vulgare*), Miners lettuce (*Claytonia perfoliata*), Texas Bullnettle (*Cnidoscolus texanus*), Bastard Toadflax (*Comandra umbellata*), Dayflower (*Commelina*), Spreading Dayflower (*Commelina diffusa*), Poison hemlock (*Conium maculatum*), Bindweed, Field (*Convolvulus arvensis*), Bindweed, Texas (*Convolvulus equitans*), Bindweed, Hedge (*Convolvulus sepium*), Horseweed (*Conyza canadensis*), Rain Lily (*Cooperia drummondii*), Coreopsis (*Coreopsis tinctoria*), swinecress (*Coronopus didymus*), Scrambledeggs (*Corydalis curvisiliqua*), Croton, Woolly (*Croton capitatus*), Croton, Tropic (*Croton glandulosus*), Croton, Texas (*Croton texensis*), Buffalo Gourd (*Cucurbita foetidissima*), Field Dodder (*Cuscuta campestris*), Marsh Parsley (*Cyclospermum leptophylum*), Nutsedge, yellow (*Cyperus esculentus*), Jimsonweed (*Datura stramonium*), Wild Carrot (*Daucus carota*), Tansymustard (*Descurainia pinnata*), Flixweed (*Descurainia sophia*), Illinois Bundleflower (*Desmanthus illinoensis*), Creeping Beggarweed (*Desmodium incanum*), Beggarweed (*Desmodium* spp.), Dichondra (*Dichondra repens*), Crabgrass, large (*Digitaria sanguinalis*), Barnyard grass (*Echinochloa crusgalli*), False Daisy or Eclipta (*Eclipta prostrata*), Cupid's Shaving Brush (*Emilia sonchifolia*), Englemann Daisy (*Englemannia pinnatifida*), Daisy Fleabane (*Erigeron annuus*), Filaree, California or Redstem (*Erodium cicutarium*), Filaree, Texas or Storkbill (*Erodium texanum*), Garden Rocket (*Eruca vesicaria* ssp. *sativa*), Wright Eryngo (*Eryngium heterophyllum*), Rattlesnake master (*Eryngium yuccifolium*), Bushy wallflower/Treacle mustard (*Erysimum repandum*), White Snakeroot (*Eupatorium rugosum*), Dogfennel (*Euphorbia capillifolium*), Spurge, Toothed (*Euphorbia dentata*), Spurge, Leafy (*Euphorbia esula*), Spurge, Prostrate (*Euphorbia humistrata*), Snow-on-the-mountain (*Euphorbia marginata*), Nodding Spurge (*Euphorbia nutans*), Ground Spurge (*Euphorbia prostrata*), Common buckwheat (*Fagopyrum esculentum*), Indian Blanket (*Gaillardia pulchella*), Galinsoga(*Galinsoga parviflora*), Catchweed Bedstraw (*Galium aparine*), Scarlet Gaura (*Gaura coccinea*), Lizardtail Gaura (*Gaura Parviflora*), Wild *Geranium*/Carolina *geranium* (*Geranium carolinanum*), Red Homedpoppy (*Glaucium corniculatum*), Wandering Cudweed (*Gnaphalium pensylvanicum*), Curlycup Gumweed (*Grindelia squarrosa*), Annual Broomweed (*Gutierrezia dracunculoides*), Common Sneezeweed (*Helenium amarum*), Bitterweed, Brown (*Helenium badium*), Smallhead Sneezeweed (*Helenium microcephalum*), Wild sunflower (*Helianthus annuus*), Texas Blueweed (*Helianthus ciliaris*), Jerusalem Artichoke (*Helianthus tuberosus*), Camphorweed (*Heterotheca subaxillaris*), Venice Mallow (*Hibiscus trionum*), Hogpotato (*Hoffmanseggia densiflora*), Japanese Hops (*Humulus japonicus*), Waterpod (*Hydrolea quadrivalvis*), Woollywhite, Yellow (*Hymenopappus flavescens*), Woollywhite, Chalkhill (*Hymenopappus tenuifolius*), Bitterweed (*Hymenoxys odorata*), Balsam Gourd (*Ibervillea lindheimeri*), Creeping Indigo (*Indigofera spicata*), Sweetpotato (*Ipomea batatas*), Morningglory, Ivyleaf (*Ipomoea hederacea*), Morningglory, entireleaf (*Ipomoea hederacea* var. *integriuscula*), Morningglory, pitted (*Ipomoea lacunosa*), Momingglory, Bigroot (*Ipomoea pandurata*), Morningglory, Tall (*Ipomoea purpurea*), Momingglory, Sharppod (*Ipomoea trichocarpa*), Marsh elder (*Iva annua*), Russian thistle (*Kali tragus*), Hairy Caltrop (*Kallstroemia hirsutissina*), Kochia (*Kochia scoparia*), prickly lettuce (*Lactuca serriola*), Wild Lettuce (*Lactuca virosa*), Henbit (*Lamium amplexicaule*), Deadnettle, Purple (*Lamium purpureum*), Lantana (*Lantana camara*), clasping pepperweed (*Lepidium perfoliatum*), Cress (*Lepidium sativum*), Virginia Pepperweed (*Lepidium virginicum*), Bladderpod (*Lesquerella gracilis*), Corn Gromwell (*Lithospermum arvense*), Honeysuckle (*Lonicera* spp.), Birdsfoot Trefoil (*Lotus corniculatus*), Long Fruited Primrose-Willow (*Ludwigia octovalvis*), Skeletonweed (*Lygodesmia juncea*), Purple Loosestrife (*Lythrum salicaria*), Tahoka Daisy (*Machaeranthera tanacetifolia*), Common Mallow (*Malva neglecta*), Little mallow (*Malva parviflora*), Alkali Mallow (*Malvella leprosa*), Horehound (*Marrubium vulgare*), pineappleweed (*Matricaria discoidea*), Scentless chamomile/mayweed (*Matricaria maritima*), Wild chamomile (*Matricaria matricarioides*), Bur Clover (*Medicago hispida*), Black Medic (*Medicago lupulina*), Blackfoot Daisy (*Melampodium leucanthum*), Yellow Sweetclover (*Melilotus indica*), Creeping Cucumber (*Melothria pendula*), annual mercury (*Mercurialis annua*), Climbing Hempweed (*Mikania scandens*), Carpetweed (*Mollugo verticillata*), Balsam-Apple (*Momordica charantia*), Purple Horsemint (*Monarda citriodora*), Mousetail (*Myosurus minimus*), Waterleaf (*Nama hispidum*), Scarlet Musk Flower (*Nyctaginia capitata*), Cutleaf Eveningprimose (*Oenothera laciniata*), Thistle, Scotch (*Onopordum acanthium*), Prickly Pear (*Opuntia* spp.), Creeping Woodsorrel (*Oxalis comiculata*), Fall *Panicum*(*Panicum dichotomiflorum*), Florida Pellitory (*Parietaria floridana*), Santa Maria or *Parthenium* Pancake Weed (*Parthenium hysterophorus*), Virginia Creeper (*Parthenocissus quinquefolia*), African Rue (*Peganum Harmala*), White Foxglove Beardtongue (*Penstemon digitalis*), Green smartweed (*Persicaria lapathifolia*), Lady's Thumb (*Persicaria maculos*), Match-Head (*Phyla nodiflora*), Chamberbitter (*Phyllanthus urinaria*), Cutleaf Groundcherry (*Physalis angulata*), Clammy Groundcherry (*Physalis heterophylla*), Purple Flower Groundcherry (*Physalis lobata*), Smooth Groundcherry (*Physalis subglabrata*), Common Pokeweed (*Phytolacca americana*), Bracted Plantain (*Plantago aristata*), Buckhorn Plantain (*Plantago lanceolata*), Blackseed Plantain (*Plantago rugelii*), Broadleaf Plantains (*Plantago* spp.), Saltmarsh Fleabane (*Pluchea odorata*), Silversheath Knotweed (*Polygonum argyrocoleon*), Prostrate Knotweed (*Polygonum aviculare*), Wild buckwheat (*Polygonum convolvulus*), Erect knotweed (*Polygonum erectum*), Smartweed, Pale (*Polygonum lapathifolium*), Pennsylvania smartweed (*Polygonum pensylvanicum*), Smartweed, ladysthumb (*Polygonum persicaria*), knotweed (*polygonum* spp.), Common Purslane (*Portulaca oleracea*), Cinquefoil (*Potentilla recta*), Sawtooth aster (*Prionopsis ciliata*), Devil's Claw (*Proboscidea louisianica*), Mock Bishop's Weed (*Ptilimnium capillaceum*), Kudzu (*Pueraria lobata*), Carolina False Dandelion (*Pyrrhopappus carolinianus*), Smallflower buttercup (*Ranunculus abortivus*), Bulbous Buttercup (*Ranunculus bulbosus*), creeping buttercup (*Ranunculus repens*), bur buttercup (*Ranunculus testiculatus*), wild radish (*Raphanus raphanistrum*), common radish (*Raphanus sativus*), Mustard, Turnip Weed (*Rapistrum rugosum*), Mexicanhat (*Ratibida columnaris*), Smooth Sumac (*Rhus glabra*), Pusley, Florida (*Richardia scabra*), Multiflora rose (*Rosa multiflora*), Curly Dock (*Rumex crispus*), broadleaf dock (*Rumex obtusifolius*), tumble (*Salsola kali*), Lanceleaf Sage (*Salvania reflexa*), Elderberry (*Sambucus canadensis*), annual knawel (*Scleranthus annuus*), Butterweed (*Senecio glabellus*), Threadleaf Groundsel (*Senecio longilobus*), Riddell Groundsel (*Senecio riddellii*), Common Groundsel (*Senecio vulgaris*), Sicklepod (*Senna obtusifolia*), Twinleaf Sennia (*Senna roemeriana*), Hemp Sesbania (*Sesbania exaltata*), Green Foxtail (*Setaria viridis*), Burcucumber (*Sicyos angulatus*), Southern Sida (*Sida acuta*), Prickly Sida/Teaweed (*Sida spinosa*), conical catchfly (*Silene conoidea*), Nightflowering catchfly (*Silene noctiflora*), Rosinweed (*Silphium integrifolium*), Compass Plant (*Silphium laciniatum*), Cup Plant (*Silphium perfoliatum*), Thistle, Blessed Milk (*Silybum marianum*), wild mustard (*Sinapis arvensis*), Tumble/Jim Hill mustard (*Sisymbrium altissimum*), London rocket (*Sisymbrium irio*), Greenbriar (*Smilax* spp.), Black Nightshade (*Solanum americanum*), Horsenettle (*Solanum carolinense*), Silverleaf Nightshade (*Solanum elaeagnifolium*), Nightshade, black (*Solanum nigrum*), Nightshade, Eastern black (*Solanum ptycanthum*), Buffalobur (*Solanum rostratum*), Hairy Nightshade (*Solanum sarrachoides*), Potatoes, volunteer (*Solanum* spp.), Goldenrod (*Solidago* spp.), Spiny Sowthistle (*Sonchus asper*), Annual Sowthistle (*Sonchus oleraceus*), Corn spurry (*Spergula arvensis*), Bushy Buttonweed (*Spermacoce assurgens*), Orange Globe Mallow (*Sphaeralcea occidentalis*), Common Chickweed (*Stellaria media*), Dandelion (*Taraxacum officinale*), Germander (*Teucrium cubense*), Greenthread (*Thelesperma filifolium*), Field pennycress (*Thlaspi arvense*), Gray Tidestrom (*Tidestromia lanuginosa*), Hedge Parsley (*Torilis arvensis*), Western Salsify (*Tragopogon dubuis*), Horse purslane (*Trianthema portulacastrum*), Puncturevine (*Tribulus terrestris*), Coat Buttons (*Tridax procumbens*), Alsike Clover (*Trifolium hybridum*), False chamomile (*Tripleurospermum perforatum*), Broadleaf signalgrass (*Urochloa platyphylla*), Cowcockle (*Vaccaria pyramidata*), Common Mullein (*Verbascum thapsus*), Dakota Verbena (*Verbena bipinnatifida*), Cowpen Daisy (*Verbesina encelioides*), Corn Speedwell (*Veronica arvensis*), Creeping Speedwell (*Veronica filiformis*), Purslane Speedwell (*Veronica peregrina*), Vetch (*Vicia* spp.), Volunteer adzuki bean (*Vigna angularis*), Volunteer lentils, Volunteer peas, Common Cocklebur (*Xanthium strumarium*), Asiatic Hawksbeard (*Youngia japonica*).

Preferably, such weeds include: *Abutilon* spp., *Amaranthus* spp., *Brassica* spp., *Chenopodium* spp., *Datura* spp., *Helianthus* spp., *Polygonum* spp., *Rumex* spp., *Solanum* spp., *Stellaria* spp., *Ambrosia* spp., *Amsinckia* spp., *Anthemis* spp., *Capsella* spp., *Cerastium* spp., *Conyza* spp., *Ipomoea* spp., *Matricaria* spp., *Persicaria* spp.

More preferably, such weeds include: Velvetleaf (*Abutilon theophrasti*), Palmer amaranth (*Amaranthus palmeri*), Redroot Pigweed (*Amaranthus retroflexus*), Wild mustard (*Brassica kaber*), Common lambsquarters (*Chenopodium album*), Jimsonweed (*Datura stramonium*), Wild sunflower (*Helianthus annuus*), Wild buckwheat (*Polygonum convolvulus*), Pennsylvania smartweed (*Polygonum pensylvanicum*), Curly dock (*Rumex crispus*), Hairy Nightshade (*Solanum sarrachoides*), Common chickweed (*Stellaria media*), Common ragweed (*Ambrosia artemisiifolia*), Tarweed fiddleneck (*Amsinckia lycopsoides*), Corn chamomile (*Anthemis arvensis*), Shepherd's purse (*Capsella bursa-pastoris*), Mouse-ear chickweed (*Cerastium vulgatum*), Horseweed (*Conyza canadensis*), Morningglory, ivyleaf (*Ipomoea hederacea*), Wild chamomile (*Matricaria matricarioides*), Lady's Thumb (*Persicaria maculos*).

The total amount of (A) and (B) is from 5% to 99% by weight of the composition.

The crystalline modification I of mesotrione may be present in the synergistic herbicidal composition of the present invention in any suitable amount, and is generally present in an amount of from about 1% to about 90% by weight of the composition, preferably from about 1% to 80% by weight, more preferably from about 1% to about 70% by weight of the composition.

The crystalline modification I of thifensulfuron-methyl may be present in the synergistic herbicidal composition in any suitable amount, and is generally present in an amount of from about 0.1% to about 90% by weight of the composition, preferably from about 1% to about 80% by weight, more preferably from about 1% to about 70% by weight of the composition, more preferably from about 1% to about 60%.

(A) and (B) may be employed in the composition, method or use of the present invention in any suitable weight ratio. The weight ratio of the crystalline modification I of mesotrione and the crystalline modification I of thifensulfuron-methyl in the composition may be in the range of from about 150:1 to about 1:50, preferably from about 100:1 to about 1:25, more preferably from about 50:1 to about 1:10, more preferably still from about 15:1 to about 1:3, preferably from about 10:1 to about 1:1, about 7.5:1 to about 1:1, about 3.75:1 to about 1:1, most preferably 10:1.

In general, the application rate of the active ingredients depends on such factors as the type of weed, type of crop plant, soil type, season, climate, soil ecology and various other factors. The application rate of the composition for a given set of conditions can readily be determined by routine trials.

In general the composition or the method of the present invention can be applied at an application rate of from about 0.005 kilograms/hectare (kg/ha) to about 5.0 kg/ha of the total amount of active ingredient (A) and (B) being applied. Preferably, the application rate is from about 0.01 kg/ha to 3.0 kg/ha of the active ingredients.

Preferably, the application rate of the active ingredients is from 1 to 1000 g/ha of (A) the crystalline modification I of mesotrione and from 1 to 250 g/ha of (B) the crystalline modification I of thifensulfuron-methyl. More preferably, the application rate of the active ingredients is from 1 to 250 g/ha of (A) the crystalline modification I of mesotrione and from 1 to 100 g/ha of (B) the crystalline modification I of thifensulfuron-methyl. Even more preferably, the application rate of the active ingredients is from 1 to 200 g/ha of (A) the crystalline modification I of mesotrione and from 1 to 80 g/ha of (B) the crystalline modification I of thifensulfuron-methyl.

As noted above, in an embodiment of the invention, (A) the crystalline modification I of mesotrione and (B) the crystalline modification I of thifensulfuron-methyl may be applied either separately or combined as part of a two-part herbicidal system, such as the composition of the present invention. The composition is applied pre-planting, pre-emergence and/or post-emergence.

The compositions of an embodiment of this invention can be formulated in conventional manner, for example by mixing (A) the crystalline modification I of mesotrione and (B) the crystalline modification I of thifensulfuron-methyl with appropriate auxiliaries. Suitable auxiliaries will depend upon such factors as the type of formulation and will be known to the person skilled in the art.

In particular, the composition may further comprise one or more auxiliaries selected from extenders, carriers, solvents, surfactants, stabilizers, anti-foaming agents, anti-freezing agents, preservatives, antioxidants, colorants, thickening agents, solid adherents, fillers, wetting agents, dispersing agents, lubricants, anticaking agents and diluents. Such auxiliaries are known in the art and are commercially available. Their use in the formulation of the compositions of the present invention will be apparent to the person skilled in the art.

Suitable formulations for applying a combination of (A) and (B) include water-soluble concentrates (SL), emulsifiable concentrates (EC), emulsions, oil in water (EW), microemulsions (ME), suspension concentrates (SC), oil-based suspension concentrates (OD), flowable suspensions (FS), water-dispersible granules (WG), water-soluble granules (SG), wettable powders (WP), water soluble powders (SP), granules (GR), encapsulated granules (CG), fine granules (FG), macrogranules (GG), aqueous suspo-emulsions (SE), capsule suspensions (CS) and microgranules (MG). Preferred formulations are suspension concentrates (SC), water-dispersible granules (WG) and water-soluble granules (SG).

The composition may comprise one or more inert fillers. Such inert fillers are known in the art and available commercially. Suitable fillers include, for example, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates. Suitable inert fillers for granules include, for example, crushed and fractionated natural minerals, such as calcite, marble, pumice, sepiolite, and dolomite, or synthetic granules of inorganic and organic ground materials, as well as granules of organic material, such as sawdust, coconut husks, corn cobs, and tobacco stalks, and mixtures thereof.

The composition may optionally include one or more surfactants which are preferably non-ionic, cationic and/or anionic in nature and surfactant mixtures which have good emulsifying, dispersing and wetting properties, depending upon the active compound/compounds being formulated. Suitable surfactants are known in the art and are commercially available.

Suitable anionic surfactants can be both so-called water-soluble soaps and water-soluble synthetic surface-active compounds. Soaps which may be used include the alkali metal, alkaline earth metal or substituted or unsubstituted ammonium salts of higher fatty acid ($C_{10}$ to $C_{22}$), for example the sodium or potassium salt of oleic or stearic acid, or of natural fatty acid mixtures.

The surfactant may comprise an emulsifier, dispersant or wetting agent of ionic or nonionic type. Examples of such agents include salts of polyacrylic acids, salts of lignosulphonic acid, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, and phosphoric esters of polyethoxylated phenols or alcohols.

The presence of at least one surfactant is generally required when the active compound and/or the inert carrier and/or auxiliary/adjuvant are insoluble in water and the vehicle for the final application of the composition is water.

The composition may optionally further comprise one or more polymeric stabilizers. Suitable polymeric stabilizers that may be used in the present invention include, but are not limited to, polypropylene, polyisobutylene, polyisoprene, copolymers of monoolefins and diolefins, polyacrylates, polystyrene, polyvinyl acetate, polyurethanes or polyamides. Suitable stabilizers are known in the art and commercially available.

The surfactants and polymeric stabilizers mentioned above are generally believed to impart stability to the composition, in turn allowing the composition to be formulated, stored, transported and applied.

Suitable anti-foaming agents for use in the compositions include all substances which can normally be used for this purpose in agrochemical compositions. Suitable anti-foaming agents are known in the art and are available commercially. Particularly preferred antifoam agents are mixtures of polydimethylsiloxanes and perfluroalkylphosphonic acids, such as the silicone anti-foaming agents available from GE or Compton.

Suitable solvents for use in the compositions may be selected from all customary organic solvents which thoroughly dissolve the active compounds employed. Again, suitable organic solvents for (A) and (B) are known in the art. The following may be mentioned as being preferred: N-methyl pyrrolidone, N-octyl pyrrolidone, cyclohexyl-1-pyrrolidone; and a mixture of paraffinic, isoparaffinic, cycloparaffinic and aromatic hydrocarbons (available commercially as SOLVESSO™200). Suitable solvents are commercially available.

Suitable preservatives include all substances which can normally be used for this purpose in agrochemical compositions of this type and again are well known in the art. Suitable examples that may be mentioned include PREVENTOL® (from Bayer AG) and PROXEL® (from Bayer AG).

The compositions may comprise an antioxidant. Suitable antioxidants are all substances which can normally be used for this purpose in agrochemical compositions, as is known in the art. Preference is given to butylated hydroxytoluene.

Suitable thickening agents for use in the compositions include all substances which can normally be used for this purpose in agrochemical compositions. Examples include xanthan gum, PVOH, cellulose and its derivatives, clay hydrated silicates, magnesium aluminum silicates or a mixture thereof. Again, such thickening agents are known in the art and available commercially.

The compositions may further comprise one or more solid adherents. Such adherents are known in the art and available commercially. They include organic adhesives, including tackifiers, such as celluloses of substituted celluloses, natural and synthetic polymers in the form of powders, granules, or lattices, and inorganic adhesives such as gypsum, silica, or cement.

In addition, depending upon the formulation, the composition according to the invention may also comprise water.

The formulated composition may for example be applied in spray form, for example employing appropriate dilutions using a diluent, such as water.

In the method and use of an embodiment of the invention, the combination of the active ingredients can be applied to the locus where control is desired, such as to the leaves of plants and/or the surrounding soil, by a convenient method.

In the event, (A) and (B) are applied simultaneously in an embodiment of the invention, they may be applied as a composition containing (A) and (B), in which case (A) and (B) can be obtained from a separate formulation source and mixed together (known as a tank-mix, ready-to-apply, spray broth, or slurry), optionally with other pesticides, or (A) and (B) can be obtained as a single formulation mixture source (known as a pre-mix, concentrate, formulated compound (or product)), and optionally mixed together with other pesticides.

In a preferred embodiment, the method and use of the present invention employ a composition according to the present invention.

The compositions according to an embodiment of the invention are distinguished by the fact that they are especially well tolerated by crop plants being treated and are environmentally friendly.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined by the appended claims.

Embodiments of the present invention will now be described, for illustrative purposes only, by way of the following examples.

EXAMPLES

Example 1—Preparation of the Crystalline Modification I Mesotrione

The crystalline modification I of mesotrione was prepared according to the method as mentioned in WO2006021743.

Mesotrione enolate suspension was filtered to remove any excess solid enolate. 50 mL of the filtered solution was placed in a reaction flask and heated to 40° C. The pH of the solution was adjusted to 2.8 by adding 10% HCl over 20 minutes. The crystals were allowed to stir for 20 minutes before isolation by filtration. The crystals were then washed with water and sucked dry on the filter.

Example 2—Preparation of the Crystalline Modification II Mesotrione

The crystalline modification II of mesotrione was prepared according to the method as mentioned in WO2006021743.

Mesotrione crystals were stirred with water in a reaction flask. The pH was increased to 12 by adding NaOH. 1.5 mL of 10% HCl was added over 15 minutes to reduce the pH of the solution to pH 4. Crystals were obtained.

Example 3—Preparation of Amorphous Thifensulfuron-Methyl in Accordance with the Disclosure of U.S. Pat. No. 4,481,029, Example 5 with Modification Thifensulfuron-methyl in an amorphous form was prepared according to a method mentioned in U.S. Pat. No. 4,481,029.

To 2.3 g of 2-amino-4-methoxy-6-methyl-1,3,5-triazine in 30 ml of anhydrous methylene chloride was added with stirring 4.5 g of methyl 3-(N-(methoxycarbonyl)sulfamoyl)thiophene-2-carboxylate. The mixture was heated to the boiling point and allowed to cool and stir at ambient temperature for sixteen hours. The solid thus obtained was removed by filtration to yield the crude desired product.

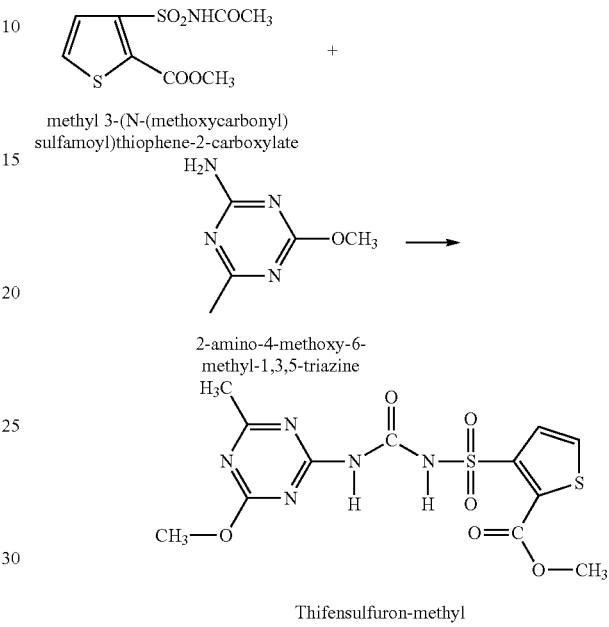

Scheme 1. Synthesis of Thifensulfuron-methyl

Figure 4:
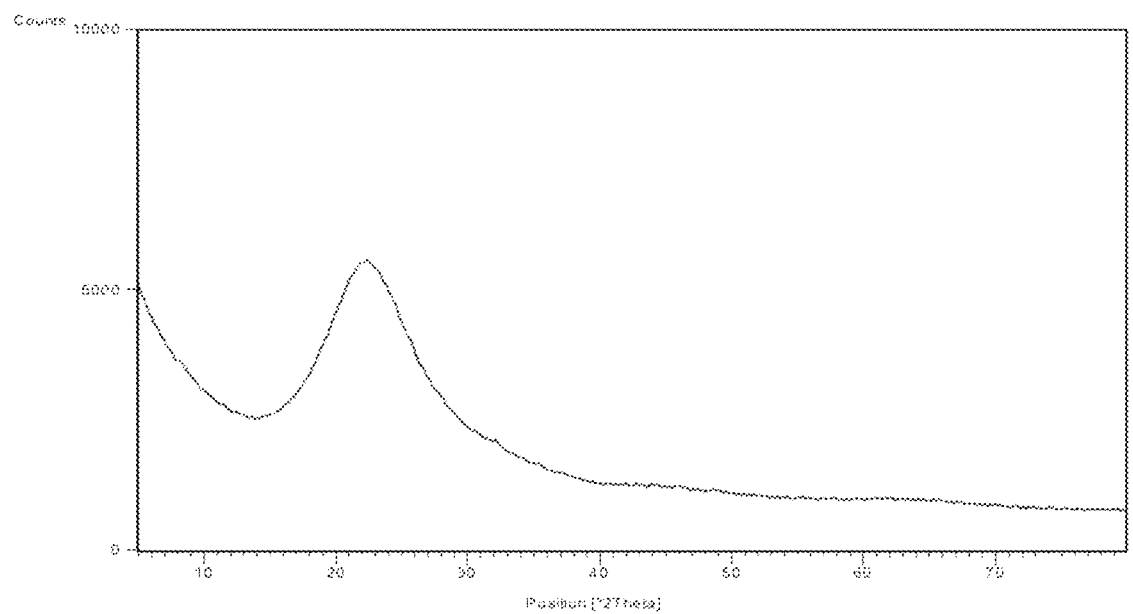
FIG. 4 is an X-ray powder diffractogram of amorphous thifensulfuron-methyl.

As shown in FIG. 4, the X-ray powder diffraction pattern of the resulting thifensulfuron-methyl product has no significant individual signals or peaks, which indicates the thifensulfuron-methyl product prepared in accordance with the disclosure of U.S. Pat. No. 4,481,029 is amorphous.

Example 4—Preparation of the Crystalline Modification I of Thifensulfuron-Methyl (Crystallization from Isopropanol)

Thifensulfuron-methyl sample prepared in Example 3 (10 g) was taken in a three-necked round bottom flask along with isopropanol (60 mL) and the resulting slurry was heated to 70° C. to get a homogeneous solution. The insoluble particles, if any, were filtered and the solution was slowly cooled to room temperature. Upon cooling, fine crystals were formed and the heterogeneous mixture was stirred at room temperature for 2 h. Then, the slurry was filtered and washed with isopropanol (3 mL). The filtered crystals were dried under vacuum at 60° C. in order to remove the isopropanol traces from the crystalline product. The crystalline product thus obtained had a purity of >98% and the recovered yield was not less than 80%.

Figure 2:
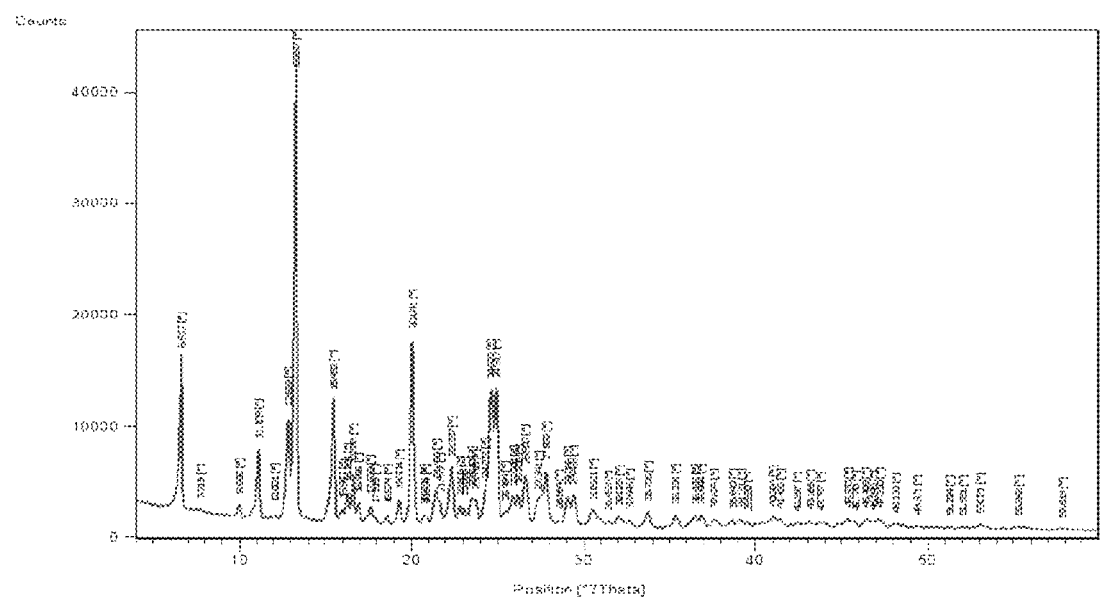
FIG. 2 is an X-ray powder diffractogram (XRD) of crystalline modification I of thifensulfuron-methyl, according to an embodiment of the invention.
Figure 3:
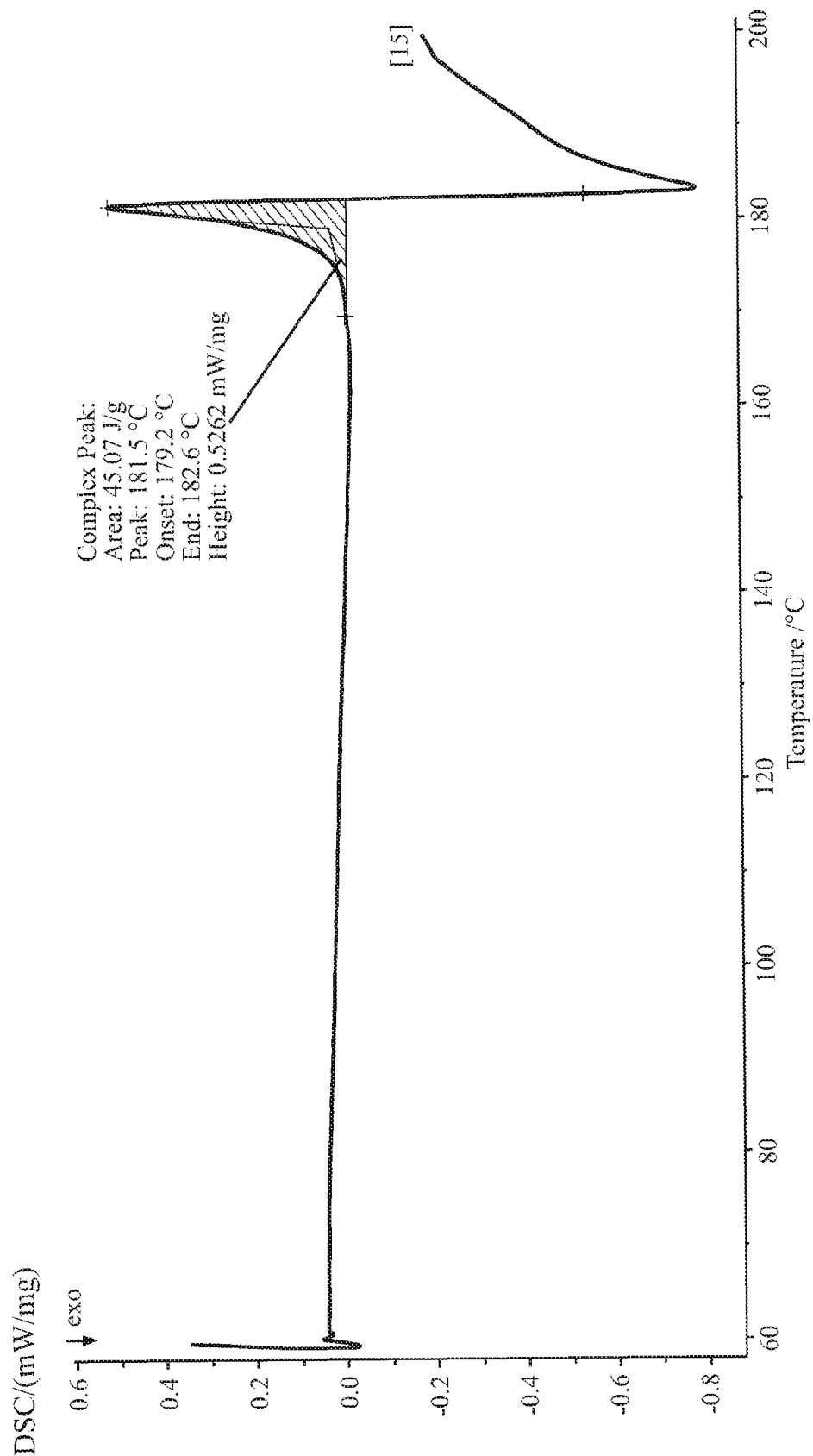
FIG. 3 is a Differential Scanning Calorimetry (DSC) thermogram of an embodiment of crystalline modification I of thifensulfuron-methyl.

The obtained crystal was analyzed by IR, X-ray powder diffraction and DSC, and found to be crystalline modification I of thifensulfuron-methyl as shown in FIGS. 1, 2 and 3, respectively.

Differential scanning calorimetry (DSC) (FIG. 3) shows an endothermic peak with onset at about 179.2° C. and peak maximum at about 181.05° C. as shown in FIG. 3.

IR spectrum of thifensulfuron-methyl shows the functional group characteristic vibrations at about 3293.22, 3075.76 and 1728.23 cm$^{-1}$ as shown in FIG. 1.

Powder X-ray diffractogram of has the reflexes as shown in FIG. 2 with reflexes summarized are summarized in Table 1 below. The X-ray powder diffractogram was taken using a diffractometer from in reflection geometry in the range from 3°-60° with increments of 0.03° using Cu—Kα radiation at 25° C.

TABLE 1

X-ray powder diffractogram reflexes of crystalline modification I of thifensulfuron-methyl crystalline modification I

| 2 θ (°) | d (Å) |
|---|---|
| 6.62 ± 0.2 | 13.67 ± 0.05 |
| 11.11 ± 0.2 | 8.46 ± 0.05 |
| 12.84 ± 0.2 | 8.03 ± 0.05 |
| 13.30 ± 0.2 | 6.32 ± 0.05 |
| 15.48 ± 0.2 | 5.63 ± 0.05 |
| 20.04 ± 0.2 | 5.31 ± 0.05 |
| 22.34 ± 0.2 | 5.22 ± 0.05 |
| 24.62 ± 0.2 | 4.22 ± 0.05 |
| 24.92 ± 0.2 | 4.00 ± 0.05 |
| 27.83 ± 0.2 | 3.82 ± 0.05 |

Example 5—Preparation of the Crystalline Modification I of Thifensulfuron-Methyl (Crystallization from n-Butanol)

Thifensulfuron-methyl (5 g) sample prepared in Example 3 was taken in a three-necked round bottom flask along with n-butanol (35 mL) and the resulting slurry was heated to 80° C. to get a homogeneous solution. The resultant hot solution was filtered to remove the insoluble (if any) and the solution was slowly cooled to ambient temperature. Product was precipitated out as fine crystal during cooling and the mixture was stirred at room temperature for 2 h. Then, the slurry was filtered, washed with n-butanol (3 mL) and dried under vacuum at room temperature in order to remove the n-butanol traces from the crystal. The crystal thus obtained was having a purity of >98% and the recovered yield was found to be not less than 80%.

The crystals were characterized as being thifensulfuron-methyl crystalline modification I using IR spectrometry, X-ray powder diffraction and DSC, as described in Example 4.

Formulation Examples

Water-dispersible granule (WG) was prepared by mixing and milling of active ingredients and auxiliaries (0.5% SUPRALATE® (sodium lauryl sulfate, Witco Inc., Greenwich), 5% REAX®88B (sodium lignosulfonate, Westvaco Corp), Potassium carbonate (balance to 100%)) under compressed air, then wetting, extruding and drying to obtain water-dispersible granule.

For example,

| | |
|---|---|
| The crystalline modification I of mesotrione | 50% |
| The crystalline modification I of thifensulfuron-methyl | 1% |
| SUPRALATE ® (sodium lauryl sulfate, Witco Inc., Greenwich) | 0.5% |
| REAX ® 88B (sodium lignosulfonate, Westvaco Corp) | 5% |
| Potassium carbonate | Balance to 100% |

Aqueous suspension concentrates (SC) were prepared by mixing finely ground active ingredients with auxiliaries (10% Propylene glycol, 5% Tristyrylphenol ethoxylates, 1% Sodium lignosulfonate, 1% Carboxymethylcellulose, 1% Silicone oil (in the form of a 75% emulsion in water), 0.1% Xanthan gum, 0.1% NIPACIDE BIT 20, Water (Balance to 1 L).

For example,

| | |
|---|---|
| The crystalline modification I of mesotrione | 40% |
| The crystalline modification I of thifensulfuron-methyl | 4% |
| Propylene glycol | 10% |
| Tristyrylphenol ethoxylates | 5% |
| Sodium lignosulfonate | 1% |
| Carboxymethylcellulose | 1% |
| Silicone oil (in the form of a 75% emulsion in water) | 1% |
| Xanthan gum | 0.1% |
| NIPACIDE BIT 20 | 0.1% |
| Water | Balance to 100% |

Water-soluble granules (SG) was prepared by mixing and milling of active ingredients and auxiliaries (0.5% SUPRALATE® (sodium lauryl sulfate, Witco Inc., Greenwich), 5% REAX®88B (sodium lignosulfonate, Westvaco Corp), 2% Sodium hydrogen carbonate ($NaHCO_3$), Potassium sulfate (balance to 100%)) under compressed air, then wetting, extruding and drying to obtain water-soluble granules.

For example,

| | |
|---|---|
| The crystalline modification I of mesotrione | 30% |
| The crystalline modification I of thifensulfuron-methyl | 4% |
| SUPRALATE ® (sodium lauryl sulfate, Witco Inc., Greenwich) | 0.5% |
| REAX ® 88B (sodium lignosulfonate, Westvaco Corp) | 5% |
| Sodium hydrogen carbonate ($NaHCO_3$) | 2% |
| Potassium sulfate | Balance to 100% |

Oil-based suspension concentrate (OD) was prepared by mixing and grinding of active ingredients and auxiliaries (7.5% Tristyrylphenol ethoxylates, 1.5% REAX®88B (Sodium lignosulfonate), 1.5% Silicon dioxide, 1.5% Silicone oil, Vegetable oil (Balance to 100%)) with a Dyno-Mill (manufactured by Willy A. Bachofen AG).

| | |
|---|---|
| The crystalline modification I of mesotrione | 15% |
| The crystalline modification I of thifensulfuron-methyl | 4% |
| Tristyrylphenol ethoxylates | 7.50% |
| REAX ® 88B (Sodium lignosulfonate) | 1.50% |
| Silicon dioxide | 1.50% |
| Silicone oil | 1.50% |
| Vegetable oil | Balance to 100% |

Formulations were prepared according to the method above (Table A):

TABLE A

| Formulation | | Mesotrione (%) | | Thifensulfuron-methyl (%) | |
|---|---|---|---|---|---|
| No. | type | I | II | Amorphous | I |
| 1 | SC | 40 | / | / | / |
| 2 | SC | / | 40 | / | / |
| 3 | WG | / | / | 60 | / |
| 4 | WG | / | / | / | 60 |
| 5 | OD | 40 | / | 4 | / |
| 6 | OD | / | 40 | 4 | / |
| 7 | SC | 40 | / | / | 4 |
| 8 | SC | / | 40 | / | 4 |
| 9 | SC | 40 | / | / | 4 |
| 10 | WG | 50 | / | / | 1 |

TABLE A-continued

| Formulation | | Mesotrione (%) | | Thifensulfuron-methyl (%) | |
|---|---|---|---|---|---|
| No. | type | I | II | Amorphous | I |
| 11 | SC | 37.5 | / | / | 1 |
| 12 | SG | 30 | / | / | 4 |
| 13 | OD | 15 | / | / | 4 |
| 14 | SC | 20 | / | / | 20 |
| 15 | SG | 10 | / | / | 30 |

Biological Examples 1

A synergistic effect exists with a combination of two active compounds when the activity of a composition comprising both active compounds is greater than the sum of the activities of the two active compounds applied individually. The expected activity for a given combination of two active compounds can be calculated by the so called "Colby equation" (see S. R. Colby, "Calculating Synergistic and Antagonistic Responses of Herbicide Combinations", Weeds 1967, 15, 20-22):

whereby:

A=the efficiency % of compound A when active compound A is employed at an application rate of m g/ha;

B=the efficiency % of compound B when active compound B is employed at an application rate of n g/ha;

E=the efficiency % of estimated activity when compounds A and B are employed together at an application rate of m g/ha and n g/ha;

then:

$$E = A + B - (A \times B/100).$$

If the actual activity observed for the combination of compounds A and B is greater than that calculated, then the activity of the combination is superadditive. In other words, synergism is present.

Wheat, barley, rye, oats and corn plants were sown side by side in the field. Different types of weeds and their relative density were recorded and are listed in Table 1 below. Formulations of Examples 1 to 8 above were applied 50 days after planting. After application, the beds were maintained for about 2 weeks. Two weeks after application, the beds were examined to determine the efficiency of the treatment. The results are set forth below in Table 2 below.

TABLE 1

| Type of weed | |
|---|---|
| Type of weed | Relative density (%) |
| Abutilon theophrasti | 15 |
| Amaranthus retroflexus | 10 |
| Chenopodium album | 10 |
| Helianthus annuus | 10 |
| Polygonum pensylvanicum | 15 |
| Solanum sarrachoides | 5 |
| Ambrosia artemisiifolia | 10 |
| Anthemis arvensis | 10 |
| Cerastium vulgatum | 5 |
| Ipomoea hederacea | 5 |
| Persicaria maculos | 5 |

TABLE 2

Efficiency (%)

| Formulation Examples | Mesotrione (g/ha) | Thifensulfuron-methyl (g/ha) | Efficiency (%) Type of weed | | | | |
|---|---|---|---|---|---|---|---|
| | | | Abutilon theophrasti | Amaranthus retroflexus | Chenopodium album | Helianthus annuus | Polygonum pensylvanicum |
| Untreated | 0 | 0 | 0 | 0 | 0 | 0 | 0 |
| Example 1 | 150 | 0 | 30 | 35 | 30 | 25 | 30 |
| Example 2 | 150 | 0 | 20 | 35 | 30 | 25 | 20 |
| Example 3 | 0 | 15 | 25 | 25 | 25 | 20 | 20 |
| Example 4 | 0 | 15 | 30 | 30 | 25 | 25 | 25 |
| Example 5 | 150 | 15 | 65 | 60 | 65 | 60 | 65 |
| Example 6 | 150 | 15 | 55 | 60 | 55 | 50 | 55 |
| Example 7 | 150 | 15 | 95 | 100 | 100 | 95 | 90 |
| Example 8 | 150 | 15 | 60 | 70 | 70 | 65 | 70 |

Efficiency (%)

| Formulation Examples | Efficiency (%) Type of weed | | | | | |
|---|---|---|---|---|---|---|
| | Solanum sarrachoides | Ambrosia artemisiifolia | Anthemis arvensis | Cerastium vulgatum | Ipomoea hederacea | Persicaria maculos |
| Untreated | 0 | 0 | 0 | 0 | 0 | 0 |
| Example 1 | 35 | 20 | 20 | 30 | 25 | 30 |
| Example 2 | 25 | 15 | 20 | 35 | 20 | 20 |
| Example 3 | 25 | 20 | 25 | 30 | 25 | 20 |
| Example 4 | 30 | 30 | 30 | 25 | 35 | 25 |
| Example 5 | 65 | 50 | 55 | 65 | 60 | 55 |
| Example 6 | 55 | 45 | 50 | 60 | 50 | 50 |
| Example 7 | 95 | 95 | 95 | 100 | 95 | 100 |
| Example 8 | 70 | 70 | 65 | 65 | 70 | 70 |

Biological Examples 2

Sorghum, soybean, sugarcane, flax and asparagus plants were sown side by side in the field. Different types of weeds and their relative density were recorded and are listed in Table 3 below. Formulations of Examples 9 to 15 above were applied 50 days after planting. After application, the beds were maintained for about 2 weeks. Two weeks after application, the beds were examined to determine the efficiency of the treatment. The results are set forth below in Table 4 below.

TABLE 3

| Type of weed | Relative density (%) |
| --- | --- |
| *Amaranthus palmeri* | 15 |
| *Brassica kaber* | 10 |
| *Datura stramonium* | 10 |
| *Polygonum convolvulus* | 10 |
| *Rumex crispus* | 15 |
| *Stellaria media* | 5 |
| *Amsinckia lycopsoides* | 10 |
| *Capsella bursa-pastoris* | 10 |
| *Conyza canadensis* | 5 |
| *Matricaria matricarioides* | 10 |

TABLE 4

| Formulation Examples | Mesotrione (g/ha) | Thifensulfuron-methyl (g/ha) | *Amaranthus palmeri* | *Brassica kaber* | *Datura stramonium* | *Polygonum convolvulus* | *Rumex crispus* |
| --- | --- | --- | --- | --- | --- | --- | --- |
| Untreated | 0 | 0 | 0 | 0 | 0 | 0 | 0 |
| Example 9 | 100 | 10 | 100 | 95 | 100 | 95 | 95 |
| Example 10 | 150 | 3 | 90 | 85 | 85 | 85 | 90 |
| Example 11 | 150 | 4 | 85 | 90 | 90 | 85 | 90 |
| Example 12 | 120 | 16 | 95 | 85 | 90 | 90 | 90 |
| Example 13 | 75 | 20 | 95 | 95 | 95 | 90 | 90 |
| Example 14 | 30 | 30 | 90 | 85 | 90 | 85 | 90 |
| Example 15 | 20 | 60 | 90 | 90 | 90 | 95 | 85 |

| Formulation Examples | *Stellaria media* | *Amsinckia lycopsoides* | *Capsella bursa-pastoris* | *Conyza canadensis* | *Matricaria matricarioides* |
| --- | --- | --- | --- | --- | --- |
| Untreated | 0 | 0 | 0 | 0 | 0 |
| Example 9 | 100 | 100 | 95 | 90 | 95 |
| Example 10 | 85 | 90 | 95 | 90 | 90 |
| Example 11 | 85 | 85 | 90 | 85 | 85 |
| Example 12 | 95 | 95 | 95 | 85 | 95 |
| Example 13 | 90 | 95 | 90 | 90 | 95 |
| Example 14 | 95 | 90 | 85 | 90 | 90 |
| Example 15 | 85 | 90 | 90 | 90 | 95 |

The invention claimed is:

1. A composition comprising a herbicidally effective amount of
   (A) the crystalline modification I of 2-(4-mesyl-2-nitrobenzoyl)cyclohexane-1,3-dione (mesotrione); and
   (B) the crystalline modification I of methyl 3-(4-methoxy-6-methyl-1,3,5-triazin-2-ylcarbamoylsulfamoyl)thiophene-2-carboxylate (thifensulfuron-methyl), wherein the crystalline modification I of thifensulfuron-methyl is crystallized using isopropanol and/or n-butanol, and the crystalline modification I of thifensulfuron-methyl exhibits each of the following reflexes as $2\theta$ values in an X-ray powder diffractogram recorded using Cu—K$\alpha$ radiation at 25° C.:

| | |
| --- | --- |
| $2\theta = 6.62 \pm 0.2$ | (1) |
| $2\theta = 11.11 \pm 0.2$ | (2) |
| $2\theta = 12.84 \pm 0.2$ | (3) |
| $2\theta = 13.30 \pm 0.2$ | (4) |
| $2\theta = 15.48 \pm 0.2$ | (5) |
| $2\theta = 20.04 \pm 0.2$ | (6) |
| $2\theta = 22.34 \pm 0.2$ | (7) |
| $2\theta = 24.62 \pm 0.2$ | (8) |
| $2\theta = 24.92 \pm 0.2$ | (9) |
| $2\theta = 27.83 \pm 0.2$ | (10). |

2. The composition according to claim 1, wherein the weight ratio of (A) to (B) is in the range of from about 150:1 to about 1:50.

3. The composition according to claim 2, wherein the weight ratio of (A) to (B) is in the range of from about 50:1 to about 1:10.

4. The composition according to claim 3, wherein the weight ratio of (A) to (B) is 10:1.

5. The composition according to claim 1, wherein the total amount of (A) and (B) is from 5% to 99% by weight of the composition.

6. The composition according to claim 5, wherein the composition comprises, by weight, from about 1% to about 90% of (A) and from about 0.1% to about 90% of (B).

7. The composition according to claim 5, wherein the composition comprises, by weight, from about 1% to about 70% of (A) and from about 1% to about 60% of (B).

8. The composition according to claim 1, further comprising one or more auxiliaries selected from the group consisting of extenders, carriers, solvents, surfactants, stabilizers, anti-foaming agents, anti-freezing agents, preservatives, antioxidants, colorants, thickening agents, solid adherents, fillers, wetting agents, dispersing agents, lubricants, anticaking agents and diluents.

9. The composition according to claim 1, further comprising a solvent, the solvent including isopropanol and/or n-butanol, and formulated as a water-soluble concentrate (SL), an emulstifiable concentrate (EC), an emulsion, oil in water (EW), a micro-emulsion (ME), a suspension concentrate (SC), an oil-based suspension concentrate (OD), a flowable suspension (FS), a water-dispersible granule (WG), a water-soluble granule (SG), a wettable powder (WP), a water soluble powder (SP), a granule (GR), an encapsulated granule (CG), a fine granule (FG), a macrogranule (GG), an aqueous suspo-emulsion (SE), a capsule suspension (CS) or a microgranule (MG).

10. A method of controlling undesirable plant growth comprising applying to the plant or to the locus thereof a herbicidally effective amount of the herbicidal composition of claim 1.

11. The method according to claim 10, wherein the plant growth is being controlled in a crop comprising cereals, sugarcane, leguminous plants, fiber plants and vegetables.

12. The method according to either of claim 10, wherein the plant growth being controlled is one or more of broadleaf weeds and grasses.

13. The method according to claim 12, wherein the plant growth being controlled is one or more of *Abutilon* spp., *Amaranthus* spp., *Brassica* spp., *Chenopodium* spp., *Datura* spp., *Helianthus* spp., *Polygonum* spp., *Rumex* spp., *Solanum* spp., *Stellaria* spp., *Ambrosia* spp., *Amsinckia* spp., *Anthemis* spp., *Capsella* spp., *Cerastium* spp., *Conyza* spp., *Ipomoea* spp., *Matricaria* spp., and *Persicaria* spp.

14. The method according to claim 10, wherein the composition is applied at an application rate of about 0.005 kilograms/hectare (kg/ha) to about 5.0 kg/ha of the total amount of active ingredient (A) and (B).

15. The method according to claim 14, wherein the composition is applied at an application rate of from 0.01 kg/ha to 3.0 kg/ha of the total amount of active ingredient (A) and (B).

16. The method according to claim 15, wherein the composition is applied at an application rate of from 1 to 1000 g/ha of (A) and from 1 to 250 g/ha of (B).

17. The method according to claim 16, wherein the composition is applied at an application rate of from 1 to 200 g/ha of (A) and 1 to 80 g/ha of (B).

18. The method according to claim 10, wherein the composition is applied pre-planting, pre-emergence and/or post-emergence.

19. A method of controlling undesirable plant growth at a locus comprising applying to the locus herbicidally effective amounts of (A) the crystalline modification I of 2-(4-mesyl-2-nitrobenzoyl)cyclohexane-1,3-dione (mesotrione) and (B) the crystalline modification I of methyl 3-(4-methoxy-6-methyl-1,3,5-triazin-2-ylcarbamoylsulfamoyl)thiophene-2-carboxylate (thifensulfuron-methyl), wherein the crystalline modification I of thifensulfuron-methyl is crystallized using isopropanol and/or n-butanol, and the crystalline modification I of thifensulfuron-methyl exhibits each of the following reflexes as 2θ values in an X-ray powder diffractogram recorded using Cu—Kα radiation at 25° C.:

| | |
|---|---|
| 2θ = 6.62 ± 0.2 | (1) |
| 2θ = 11.11 ± 0.2 | (2) |
| 2θ = 12.84 ± 0.2 | (3) |
| 2θ = 13.30 ± 0.2 | (4) |
| 2θ = 15.48 ± 0.2 | (5) |
| 2θ = 20.04 ± 0.2 | (6) |
| 2θ = 22.34 ± 0.2 | (7) |
| 2θ = 24.62 ± 0.2 | (8) |
| 2θ = 24.92 ± 0.2 | (9) |
| 2θ = 27.83 ± 0.2 | (10). |

20. The method according to claim 19, wherein the plant growth is being controlled in a crop comprising cereals, sugarcane, leguminous plants, fiber plants and vegetables.

21. The method according to claim 19, wherein (A) and (B) are applied to the locus at the same time.

22. The method according to claim 19, wherein (A) and (B) are applied to the locus consecutively.

23. The method according to claim 19, wherein the plant growth being controlled is one or more of broadleaf weeds and grasses.

24. The method according to claim 23, wherein the plant growth being controlled is one or more of *Abutilon* spp., *Amaranthus* spp., *Brassica* spp., *Chenopodium* spp., *Datura* spp., *Helianthus* spp., *Polygonum* spp., *Rumex* spp., *Solanum* spp., *Stellaria* spp., *Ambrosia* spp., *Amsinckia* spp., *Anthemis* spp., *Capsella* spp., *Cerastium* spp., *Conyza* spp., *Ipomoea* spp., *Matricaria* spp. and *Persicaria* spp.

25. The method according to claim 19, wherein the weight ratio of (A) to (B) applied is in the range of from about 150:1 to about 1:50.

26. The method according to claim 25, wherein the weight ratio of (A) to (B) applied is in the range of from about 50:1 to about 1:10.

27. The method according to claim 26, wherein the weight ratio of (A) to (B) applied is 10:1.

28. The method according to claim 19, wherein (A) and (B) are applied at an application rate of 0.005 kilograms/hectare (kg/ha) to about 5.0 kg/ha of the total amount of active ingredient (A) and (B).

29. The method according to claim 28, wherein (A) and (B) are applied at an application rate of from about 0.01 kg/ha to about 3.0 kg/ha of the total amount of active ingredient (A) and (B).

30. The method according to claim 29, wherein (A) and (B) are applied at an application rate of from 1 to 1000 g/ha of (A) and from 1 to 250 g/ha of (B).

31. The method according to claim 30, wherein (A) and (B) are applied at an application rate of from 1 to 200 g/ha of (A) and 1 to 80 g/ha of (B).

32. The method according to claim 19, wherein (A) and (B) are applied pre-planting, pre-emergence and/or post-emergence.

* * * * *